US010828166B2

(12) United States Patent
Currier et al.

(10) Patent No.: US 10,828,166 B2
(45) Date of Patent: *Nov. 10, 2020

(54) ACETABULAR COMPONENTS FOR ARTIFICIAL HIPS AND METHOD OF USE

(71) Applicant: Cornerstone Partners LLC, Norwich, VT (US)

(72) Inventors: John H. Currier, Norwich, VT (US); Zachary M. Currier, Norwich, VT (US)

(73) Assignee: Cornerstone Partners LLC, Norwich, VT (US)

(*) Notice: Subject to any disclaimer, the term of this patent is extended or adjusted under 35 U.S.C. 154(b) by 117 days.

This patent is subject to a terminal disclaimer.

(21) Appl. No.: 16/146,401

(22) Filed: Sep. 28, 2018

(65) Prior Publication Data
US 2019/0029832 A1 Jan. 31, 2019

Related U.S. Application Data

(63) Continuation of application No. 14/377,698, filed as application No. PCT/US2013/025589 on Feb. 11, 2013, now Pat. No. 10,085,840.

(60) Provisional application No. 61/597,546, filed on Feb. 10, 2012.

(51) Int. Cl.
*A61F 2/34* (2006.01)
*A61F 2/46* (2006.01)
*A61F 2/32* (2006.01)
*A61F 2/30* (2006.01)

(52) U.S. Cl.
CPC .............. *A61F 2/34* (2013.01); *A61F 2/4637* (2013.01); *A61F 2002/30014* (2013.01); *A61F 2002/30016* (2013.01); *A61F 2002/30332* (2013.01); *A61F 2002/30337* (2013.01); *A61F 2002/30495* (2013.01); *A61F 2002/30515* (2013.01); *A61F 2002/30695* (2013.01); *A61F 2002/30934* (2013.01); *A61F 2002/3241* (2013.01); *A61F 2002/4627* (2013.01); *A61F 2002/4628* (2013.01)

(58) Field of Classification Search
CPC .... A61F 2/32; A61F 2/34; A61F 2002/30515; A61F 2002/30495; A61F 2002/30497; A61F 2002/30663; A61F 2002/3208
See application file for complete search history.

(56) References Cited

U.S. PATENT DOCUMENTS

| 4,770,658 A | 9/1988 | Geremakis |
|---|---|---|
| 4,784,663 A | 11/1988 | Kenna |
| 4,795,471 A | 1/1989 | Oh |
| 5,062,853 A | 11/1991 | Forte |

(Continued)

FOREIGN PATENT DOCUMENTS

| WO | WO-03/092557 A2 | 11/2003 |
|---|---|---|
| WO | WO-2007/079521 A1 | 7/2007 |

OTHER PUBLICATIONS

Extended European Search Report for European Patent Application No. 13746376.6, dated Sep. 15, 2015 (7 pages).

(Continued)

*Primary Examiner* — Marcia L Watkins
(74) *Attorney, Agent, or Firm* — Clark & Elbing LLP

(57) ABSTRACT

The invention features acetabular components for an artificial hip. The invention also features methods and tools for assembling a hip prosthesis that includes the acetabular components of the invention.

15 Claims, 16 Drawing Sheets

Schematic showing the sequence of assembly of the bearing components into the acetabular cup.

(56) References Cited

U.S. PATENT DOCUMENTS

| | | |
|---|---|---|
| 5,092,897 A | 3/1992 | Forte |
| 5,263,988 A | 11/1993 | Huebner |
| 5,314,491 A | 5/1994 | Thongpreda et al. |
| 6,682,567 B1 | 1/2004 | Schroeder |
| 8,114,166 B2 | 2/2012 | Auxepaules et al. |
| 2005/0171614 A1 | 8/2005 | Bacon |
| 2006/0167556 A1 | 7/2006 | Lazennec et al. |

OTHER PUBLICATIONS

International Search Report and Written Opinion for International Patent Application No. PCT/US2013/25589, dated Jun. 12, 2013 (15 pages).

Schematic showing the sequence of assembly of the bearing components into the acetabular cup.

300

Install acetabular cup in
patient's acetabulum
302

Insert rim bearing into
acetabular cup
304

Insert locking component
306

Align and reduce
femoral component
308

Figure 13

ACETABULAR COMPONENTS FOR ARTIFICIAL HIPS AND METHOD OF USE

BACKGROUND

Approximately 460,000 artificial hips are implanted annually, in the United States alone. An increase in the number of younger and more physically active patients has prompted the orthopedic implant industry to develop more durable, wear-resistant bearing materials. These include metal-on-metal or ceramic-on-ceramic bearings. However, despite the large demand for low volumetric wear hard-on-hard bearings, sales of metal-on-metal bearings has declined, due to concerns about severe adverse tissue reaction to metal ions and metal debris.

Metal on metal ("MOM") hips are currently under scrutiny due to reportedly high failure rates. Recent analysis of retrieved MOM hip bearings, e.g., as described in Currier et al., *Gouge features on Metal-on-Metal hip bearings can result from high stresses during rim contact*, Tribol. Int., 2012, doi: 10.1016/jtriboint.2012.04.014; and in McHugh et al., *Plastic deformation from edge loading is common on retrieved Metal-on-Metal hips and can be predicted with finite element analysis*, JAI, 2012, doi: 10.1520/STP 156020120046 (each of which is incorporated herein by reference) shows wear and damage features that suggest edge loading of artificial hips under a variety of in vivo conditions. The edge loading effects may be associated with pain and instability in patients. Furthermore, the August 2010 recall of the ASR™ hip by DePuy has focused intense media attention, and technical and legal scrutiny of metal-on-metal bearings.

Ceramic-on-ceramic ("COC") bearings are an alternative solution. However, these bearings have also suffered a major setback over the last 4 years due to a growing incidence of in vivo squeaking. COC hips are also susceptible to edge loading. The metal rim of a conventional acetabular cup can scrape off onto a ceramic femoral head when the femoral head is reduced into the acetabular cup (and ceramic liner) during surgery. Metal on the ceramic head may be a factor in painful, unstable and/or squeaking COC hips, e.g., as described in Currier et al., *A proposed mechanism for squeaking of ceramic-on-ceramic hips*, Wear, 2010, 269: 782-789, doi: 10. 1016/jwear.2010.08.006, Elsevier B. V; and in Tomek, et al., *Metal transfer on a ceramic head with a single rim contact*, J. Arthroplasty, Vol. 27 No. 2, 2012, Elsevier, Inc., each of which is incorporated herein by reference.

Conventional artificial hips feature an intentional mismatch between the internal acetabular cup diameter and the diameter of the femoral head, in order to allow for lubrication by synovial fluid. However, this mis-match allows a roll/slide mechanism when the hip is flexed—flexion occurs by rolling and sliding of the head within the cup/liner. The roll/slide of the head in the cup has been demonstrated to cause the hip to vibrate at an audible frequency in vitro, and may also be a causative factor in squeaking hips in vivo.

Thus there is a need for developing bearing surfaces for use in hip prosthesis that address the problem of edge loading and squeaking.

SUMMARY OF THE INVENTION

The invention features an acetabular component that includes a hybrid bearing surface. The acetabular component includes: a) a polar bearing that includes an interior surface; and b) a rim bearing that also includes an interior surface. The interior surface of the polar bearing and the interior surface of the rim bearing form the hybrid bearing surface such that a distal portion of a proximal femoral head placed in its normal position contacts both the interior surface of the polar bearing and the interior surface of the rim bearing. The polar bearing and the rim bearing are shaped to fit into an acetabular cup.

In certain embodiments, the acetabular component can also include an acetabular cup. Desirably, the acetabular component includes a locking component designed to displace the rim bearing radially outward against an acetabular cup. The acetabular component can be made, for example, of materials that allow for the elastic and/or plastic deformation of the rim bearing without substantial plastic deformation of a femoral head at physiological loading (e.g., at a force of about 2000, 3000, 4000, 5000, 6000, 7000, 8000, 9000, or even 10,000 Newtons).

The invention also features an acetabular prosthesis that includes the acetabular component described above, an acetabular cup, and a locking component. In one embodiment, the polar bearing can be integral to the acetabular cup.

Desirably, the acetabular cup includes a morse taper present about an inner circumference of the acetabular cup. The acetabular cup can also include a reverse taper portion about an inner circumference of the acetabular cup. The rim bearing can include an exterior circumferential groove and an angled sidewall for fitting with the reverse tapered portion of the acetabular cup. The rim bearing can also include a lip for covering a rim of the acetabular cup.

The rim bearing can be a single component or constructed from multiple segments. The rim bearing can also include one or more locking component that can displace the rim bearing radially outward against the acetabular cup. In one embodiment, the rim bearing is in the shape of an arc to allow a reduction in effective circumference of the rim bearing and facilitate insertion of the rim bearing into the acetabular cup. The locking component can fit between the ends of an arc-shaped rim bearing to secure the rim bearing against the reverse tapered portion of the acetabular cup. The locking component can include a lip for covering the rim of the acetabular cup between the open ends of the rim bearing. In certain embodiments, the rim bearing and the polar bearing are of unitary construction.

The interior surface of the polar bearing and the interior surface of the rim bearing can form a circumferential boundary, which can be a straight or an undulating boundary. The undulating boundary can be formed, for example, by intercalation of the interior surface of the polar bearing and the interior surface of the rim bearing. The undulating boundary can also be formed by complementary interdigitation of the interior surface of the polar bearing and the interior surface of the rim bearing. A groove can be formed between the interior surface of the polar bearing and the interior surface of the rim bearing.

The acetabular cup is desirably made of a biocompatible material. The polar bearing is desirably made of a hard material and the rim bearing is desirably made of a compliant material such that the hard material is harder than the compliant material. Exemplary hard materials that can be used to make the polar bearing are metal, ceramic, a polymeric material, and cross-linked polyethylene. Exemplary compliant materials that can be used to make the rim bearing are polyethylene (PE), ultra high molecular weight polyethylene (UHMWPE), polyetheretherketone (PEEK), cross-linked UHMWPE, or polymethylmethacrylate (PMMA). Other materials known in the art can also be used. In certain embodiments, the rim bearing material allows for the elastic and/or plastic deformation of the rim bearing without substantial plastic deformation of the femoral head at physiological loading (e.g., at a force of about 2000, 3000, 4000, 5000, 6000, 7000, 8000, 9000, or even 10,000 Newtons).

Means for aligning the rim bearing and/or the locking component with the acetabular cup can be present. Such means can include, for example, a plurality of holes, notches, or indentations on the acetabular cup and one or more protrusions on the rim bearing and are locking component that are sized to mate with the holes, notches, or indentations, or vice versa. Desirably, the rim bearing is proud of other surfaces and is positioned to contact a proximal portion of the femoral head.

The invention also features methods for installing in a patient, a prosthesis that includes a hybrid bearing surface acetabular component as described above. Generally the method includes the steps of: a) installing an acetabular cup in an acetabulum of the patient; b) inserting a polar bearing into the acetabular cup; c) inserting a rim bearing into the acetabular cup such that the interior surface of the polar bearing and the interior surface of the rim bearing form the hybrid bearing surface, and d) aligning and reducing a femoral head of a femoral component such that a distal portion of the femoral head in its normal position contacts both the polar bearing and the rim bearing. The locking component can be installed after insertion of the rim bearing into the acetabular cup, but before aligning and reducing the femoral head. Alternatively, the locking component can be installed after aligning and reducing the femoral head.

The invention also features a method for installing in a patient a prosthesis that includes a hybrid bearing surface acetabular component and an apron. This method generally includes the steps of: a) installing an acetabular cup in an acetabulum of the patient; b) inserting a polar bearing into the acetabular cup; c) placing a circle or arc-shaped apron made of UHMWPE, low density PE, polyoxymethylene and its derivatives (sold commercially as, for example, Delrin™, Celcon™, or Hostaform™), polyamide and its derivatives (e.g., nylons), polypropylene, or the like about the rim of the acetabular cup; d) placing a rim bearing comprising an interior surface around a femoral neck; e) attaching a femoral head to the femoral neck to form a femoral component; f) inserting the rim bearing and the femoral component into the acetabular cup, wherein the interior surface of the polar bearing and the interior surface of the rim bearing form the hybrid bearing surface; g) aligning and reducing the femoral head of the femoral component, wherein a distal portion of the femoral head in its normal position contacts both the polar bearing and the rim bearing; h) removing the apron; i) positioning the rim bearing in the acetabular cup; and j) securing the rim bearing in the acetabular cup. The locking component can be installed after positioning the rim bearing in the acetabular cup but before securing the rim bearing in the acetabular cup.

The invention also features a rim bearing insertion tool for inserting a rim bearing above a polar bearing of an acetabular component. The tool can include: a) means for removably securing the tool to the acetabular cup; b) means for reversibly engaging the rim bearing onto the tool for placement into the acetabular cup; c) means for reducing the effective diameter of the rim bearing; d) means for inserting the rim bearing into the acetabular cup; and e) means for mutually aligning the rim bearing and a locking component to place the locking component in a location suitable for insertion and locking of the rim bearing.

In certain embodiments, the tool can also include: a base having a shape with a substantially hemispherical outline, and a frame (e.g., a frame made of stainless steel) extending from a top of the base and that serves as a handle and a manual rotational alignment mechanism. In one embodiment, the base can be of a substantially hemispherical shape and can be made of a soft material (e.g., UHMWPE or thermoplastic) relative to that of the polar bearing. The tool can further include a sliding carriage that is allowed to travel up and down the frame; and a scissors mechanism with appropriate handles such that the scissors mechanism includes downward pointing pins on a lower part and is affixed to the sliding carriage. Preferably, the base of the tool is made of a material that is of a lesser hardness than that of the polar bearing in order to avoid damage to the polar bearing during installation. Exemplary materials that can be used to make the base of the tool are PE, UHMWPE, PMMA, and polyoxymethylene and its derivatives (e.g., Delrin™). In one example, the base of the tool is stainless steel when the polar bearing is made of ceramic. The rim bearing insertion tool can be sterilized before and after surgery.

The invention also features a method of installing in a patient a prosthesis that includes a hybrid bearing surface acetabular component by using the rim bearing tool. This method generally includes: a) removably securing the tool to an acetabular cup installed in a patient; b) reversibly engaging the rim bearing onto the tool; c) reducing the effective diameter of the rim bearing; d) inserting the rim bearing into the acetabular cup; e) mutually aligning the rim bearing and a locking component; and f) placing the locking component in a suitable location to lock the rim bearing.

In certain embodiments, the method can also include: a) implanting an acetabular cup, with a polar bearing inserted, into an acetabulum of a patient; b) fitting a rim bearing with holes around a frame of the insertion tool; c) rotating the rim bearing to align with pins in the scissors mechanism and to press the rim bearing onto the pins; d) placing the insertion tool into the polar bearing; e) squeezing the scissors mechanism together to contract the rim bearing to a smaller effective diameter; f) pushing the sliding carriage down until the rim bearing is adjacent to and inside of a reverse taper on the acetabular cup; g) opening the scissors mechanism and allowing rim bearing to deflect radially outward into the reverse taper profile of the acetabular cup; h) placing a locking component on the hemispherical base; i) pushing the locking component radially outward into its opening; j) raising the travelling carriage; k) pulling the pins from the holes in the rim bearing; and l) pulling the rim bearing tool from a surgical site.

Definitions

By a "hard material" as used herein is meant a material, such as metal, oxidized metal, ceramic, or polymer that is chosen for its hardness and resistance to abrasive wear, and has a hardness of at least about 20 (e.g., at least about 25, 30, 50, 100, or more) on the Rockwell C scale (HRC) and a Young's modulus of at least about 10 (e.g., at least about 20, 50, 100, 200, 500, 1000, or more) gigapascal.

By a "compliant material" as used herein is meant a material, such as PE, UHMWPE, PEEK, and PMMA, that has a hardness of less than about 150 (e.g., less than about 140, 120, 100, 90, 70, 50, 30, 10, 1, 0.1, or less) on the Rockwell R scale (HRR) and a Young's modulus of less than about 10 (e.g., less than 9, 7, 5, 3, 1, 0.5, 0.1, 0.05, 0.01, or less) gigapascal, a value that is at least 30%, 40%, 50%, 60%, 70%, 80%, 90%, 95% or even 100% less compared to the Young's modulus of the material of the polar bearing.

By "normal position" as used herein is meant a position of the proximal femoral head when it is perpendicular to the tangent of the pole of the polar bearing.

By "elastic deformation" as used herein is meant a reversible change in the size or shape of an object (e.g., the rim bearing).

By "plastic deformation" as used herein is meant an irreversible change in the shape or size of an object.

By "physiological loading" as used herein is meant the force generated by a body's normal movements in an acetabular prosthesis, typically from about 400 to 10,000 newtons (N). The loading depends on many factors, including an individual's body weight, activity being undertaken (e.g. standing still vs. jumping) and the angle and surface of contact between the acetabular and femoral components.

BRIEF DESCRIPTION OF THE DRAWINGS

FIG. 13 is a flowchart depicting a method of installing a prosthesis where the polar bearing is integral with the acetabular cup.

DETAILED DESCRIPTION

Figure 1:
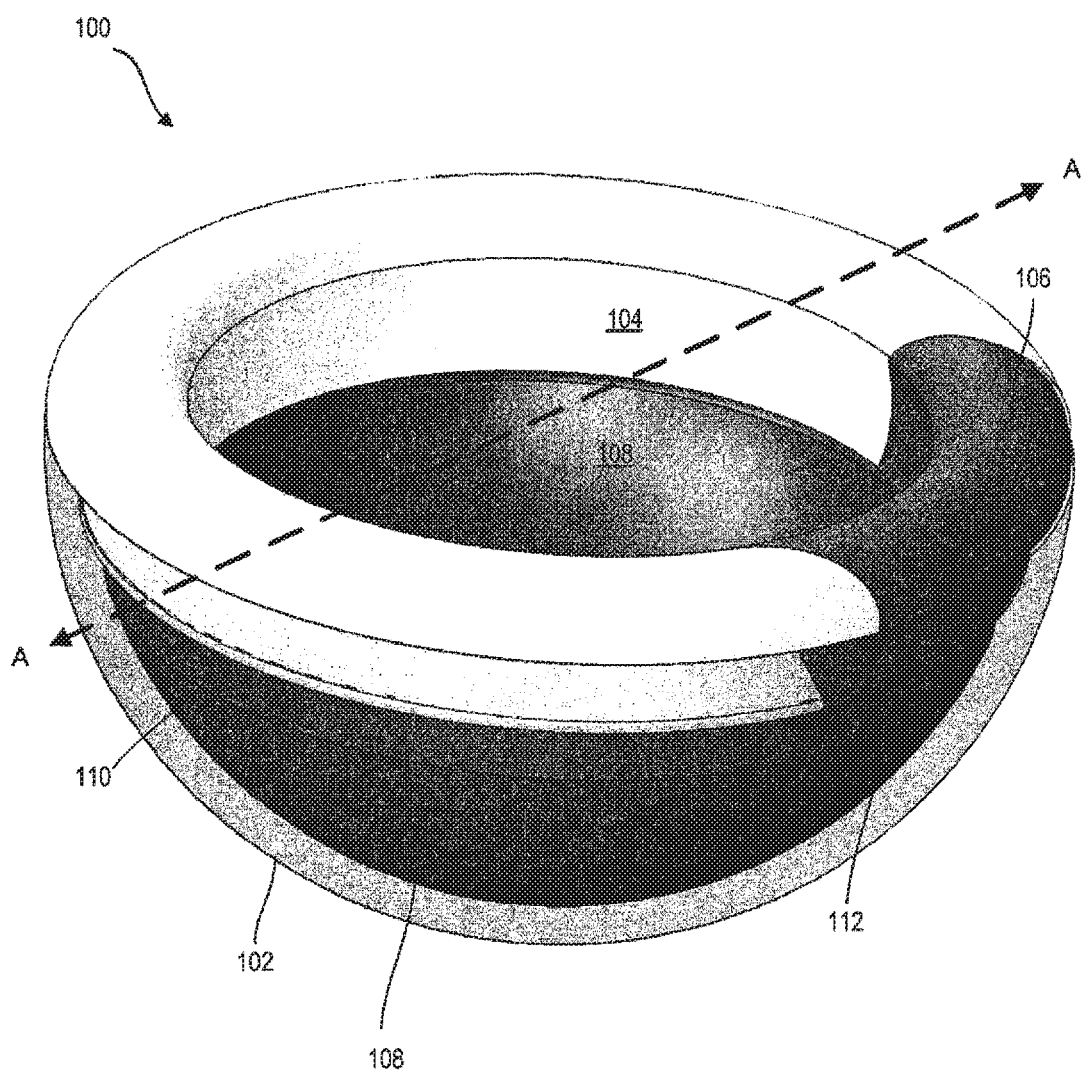
FIG. 1 is a perspective view of an acetabular component that includes an acetabular cup, a hybrid bearing surface formed by a polar bearing and a rim bearing and a locking component.

The invention features acetabular components for an artificial hip. The acetabular components can have a modular or unitary design and include an interior surface for articulation with a femoral head. The acetabular components can include a polar bearing and a rim bearing that form a hybrid bearing such that the hybrid bearing fits into an acetabular cup. The invention also features methods and tools for installing in a patient a prosthesis that includes the acetabular components of the inventions.

Acetabular Component with a Modular Hybrid Bearing Surface

The invention features an acetabular component that includes a hybrid bearing surface with a modular design that can address the problem of edge loading. The acetabular component includes a hybrid bearing 104 that can be made of a polar bearing 108 and an outer circumferential rim bearing 114. The polar bearing 108 can be made of a hard material (e.g., metal, ceramic or cross-linked PE) that is resistant to abrasive wear and the rim bearing 114 can be made of a compliant material, such as ultra high molecular weight polyethylene (e.g., PE, UHMWPE, PEEK, or PMMA). The interior surface of the polar bearing 108 and the interior surface of the rim bearing 114 to form the surface of the hybrid bearing 104. The rim bearing can also be resistant to abrasive wear. The hybrid bearing surface combines high wear resistance of the hard material in the region of the bearing where relatively high-velocity articulation occurs during gait, with compliance and toughness at and near the rim, e.g., the rim of an acetabular cup, where bearing contact occurs during gait reversal and reseating of the femoral head following micro-separation. The outer, circumferential portion may also be self-lubricating, e.g., where PE is used, and may extend over the hard acetabular cup rim to prevent contact and scraping between the hard rim and the femoral head (e.g., during reduction during surgery or reduction following any dislocation or micro-separation). This acetabular component can minimize or eliminate the detrimental tribological effects of edge loading of hard-on-hard hip arthroplasty bearings. The polar bearing may also fit more tightly against the femoral head than do conventional bearings, such that rolling of the femoral head within the polar portion of the bearing is limited or prevented, thus reducing audible squeak. The acetabular component can be made of materials that allow for the elastic and/or plastic deformation of the rim bearing without substantial plastic deformation of a femoral head at physiological loading (e.g., at a force of about 2000, 3000, 4000, 5000, 6000, 7000, 8000, 9000, or even 10,000 Newtons).

When a proximal femoral head is in its normal position such that the axis of the femoral head originating from the femoral neck and passing through the pole of the polar bearing is parallel to the axis of the polar bearing, then the distal hemisphere of the proximal femoral head can contact the interior surface of the polar bearing and the interior surface of the rim bearing. The distal hemisphere of the proximal femoral head is the hemisphere of the proximal femoral head (i.e., the head that attaches at the hip) that is farthest away from the neck of the femur. Even though one or more layers of synovial fluid can be present between the femoral head and the polar bearing and/or rim bearing, in the present context, the femoral head is considered to be in contact with the polar bearing and/or rim bearing even in the presence of synovial fluid between them.

Acetabular Component with a Hybrid Bearing Surface and an Acetabular Cup

In certain embodiments, the acetabular component also includes an exterior acetabular cup 102. The polar bearing 108 can be shaped to fit into the exterior acetabular cup 102 as shown in FIG. 1, which in turn can be fit into a patient's acetabulum. A rim bearing 114 fits into the acetabular cup, e.g., the exterior acetabular cup 102, atop a rim 111 of the polar bearing 108. FIGS. 2-7 show additional details of cup 102, polar bearing 108 and the rim bearing 114. The alignment of the exterior acetabular cup 102 relative to the polar bearing 108 and rim bearing 114 are described below.

In certain embodiments, polar bearing 108 can be inserted into an acetabular cup 102 such that an upper, circumferential edge 110 of polar bearing 108 aligns with an inner, circumferential Morse taper type profile 112 of cup 102. Morse taper profile 112 tapers slightly inward toward the pole of cup 102. The Morse taper profile can be thought as dividing the acetabular cup into a polar first chamber and an outer second chamber. The polar bearing 108 of the hybrid bearing 104 can also be less than a hemisphere. A rim bearing 114 fits into cup 102 atop a rim 111 of polar bearing 108, in particular, against an upper, internal reverse-tapered portion 116 about the upper circumference of cup 102. In other embodiments, the polar bearing and acetabular cup can be of unitary construction.

Figure 2:
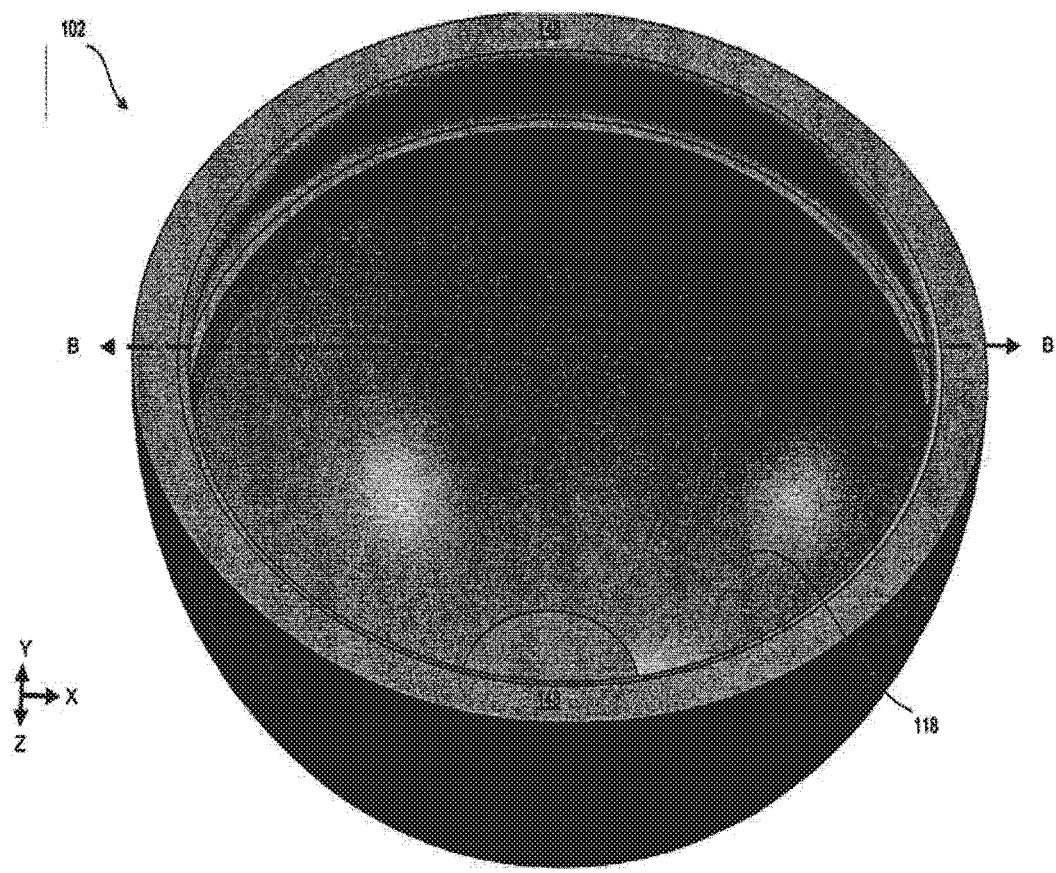
FIG. 2 is a perspective view of the acetabular cup of the hybrid bearing surface acetabular component of FIG. 1.
Figure 3:
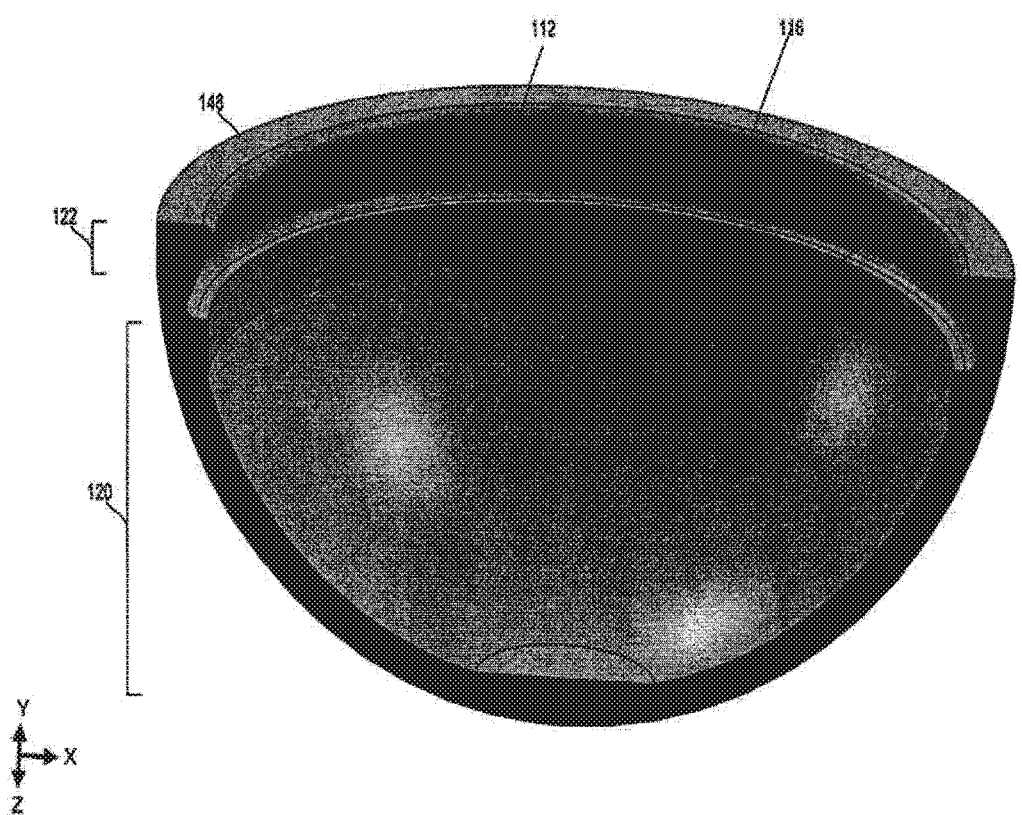
FIG. 3 is a cross-sectional view of the acetabular cup of FIGS. 1 and 2, illustrating a reverse tapered profile and taken along line B-B of FIG. 2.

As shown in FIGS. 2-3, acetabular cup 102 has a hollow interior 118 for accepting polar bearing 108. A lower chamber 120 of the cup accepts polar bearing 108. An upper chamber 122 above lower chamber 120 has a diameter greater than the largest diameter of lower chamber 120. Rim bearing 114 fits against reverse tapered portion 116 of upper chamber 122. When fitted into lower chamber 120, polar bearing 108 may form a shelf to enhance support of rim bearing 114 in upper chamber 122. Acetabular cup 102 can be affixed to a patient's acetabulum, for example, using bone cement or an ingrowth surface such as a porous coating. An exterior surface 123 of cup 102 can be roughened or textured to increase surface area available for bonding. The exterior surface 123 can be treated with hydroxyapatite or other materials that promote osseointegration.

Figure 4:
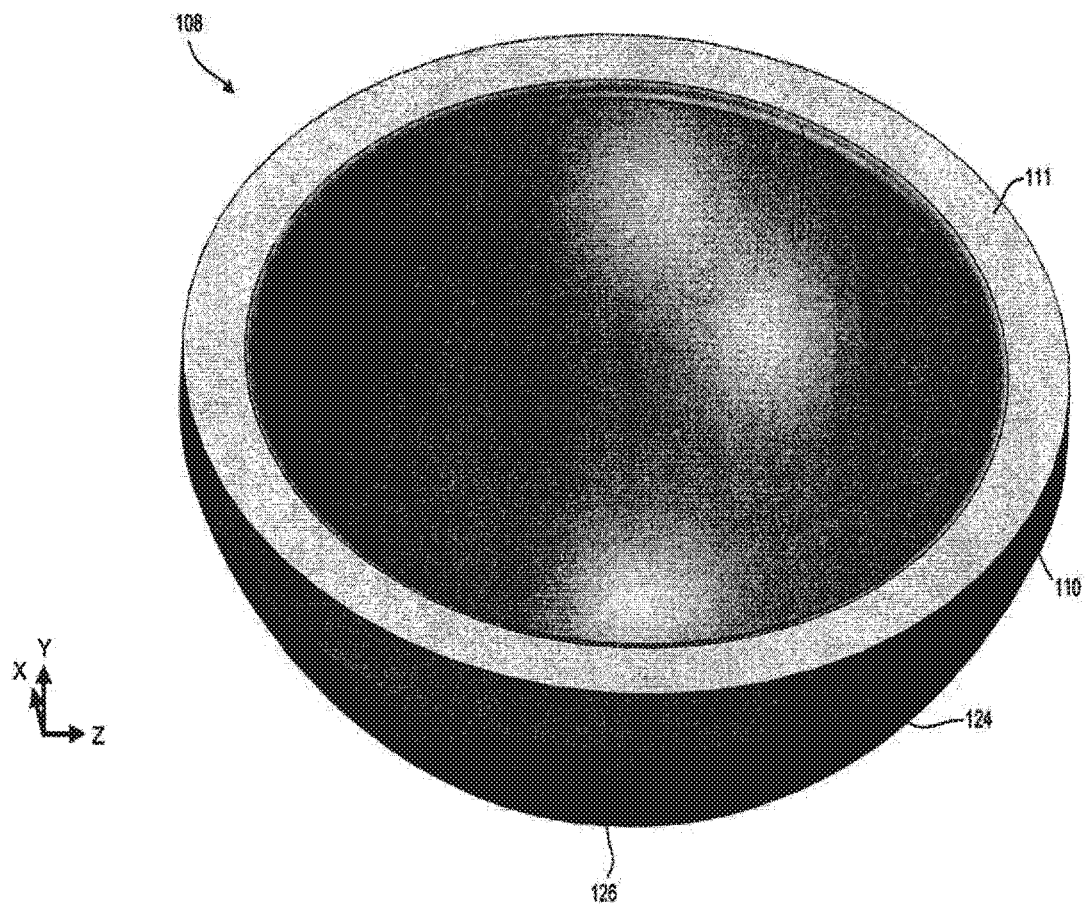
FIG. 4 is a perspective view of a polar bearing shown in FIG. 1.

FIG. 4 is a perspective view showing polar bearing 108. The edge 110 can extend upward (i.e., vertically or near vertically) from the exterior of a lower body 124 of polar bearing 108 (when body 124 stands on an end 126) and terminate in rim 111, such that, when inserted into cup 102, edge 110 fits with Morse taper profile 112 and rim 111 provides support for rim bearing 114. The angles and shapes of both polar bearing 108 and profile 112 can be altered, so long as polar bearing 108 and profile 112 are complementary. Polar bearing 108 may include a chamfered inner edge 127 between rim 111 and the interior of lower body 124. Chamfered inner edge 127 for example reduces stress concentration at the interface between polar bearing 108 and rim bearing 114 and provides a recession into which any debris can be swept from an articular surface 128 of polar bearing 108/assembled component 100. As described above, the polar bearing 108 and the interior surface of the polar bearing 108 can be made of a hard material selected from the group consisting of metal, ceramic, a polymeric material, and cross-linked PE. The polar bearing and rim bearing can be made of different materials, e.g., the polar bearing can be made of a material harder (e.g., metal, ceramic, or cross-linked PE) than the rim bearing and the rim bearing can be made of a more compliant material (e.g., PE, UHMWPE, PEEK, or PMMA).

Instead of being separate components, the polar bearing 108 and rim bearing 114 can be of unitary design in the hybrid bearing 104 and the hybrid bearing fits as one piece within the acetabular cup 102. In this case, instead of being two separate components, as described above, the polar bearing 108 and rim bearing 114 can be formed by a material having a gradient of hardness, where the gradient has decreasing hardness moving from the polar portion of the polar bearing 108 towards the rim bearing 114. For example, if the material is PE, then a gradient of hardness can be achieved by differential cross linking to make the PE harder in the polar bearing and less hard, and more compliant, in the rim bearing.

The acetabular cup 102 is preferably made of a biocompatible metal, such as titanium; however, other sufficiently strong, biocompatible materials may be utilized in addition to or as an alternative to metal.

Rim Bearing Design and Locking Component

Figure 5:
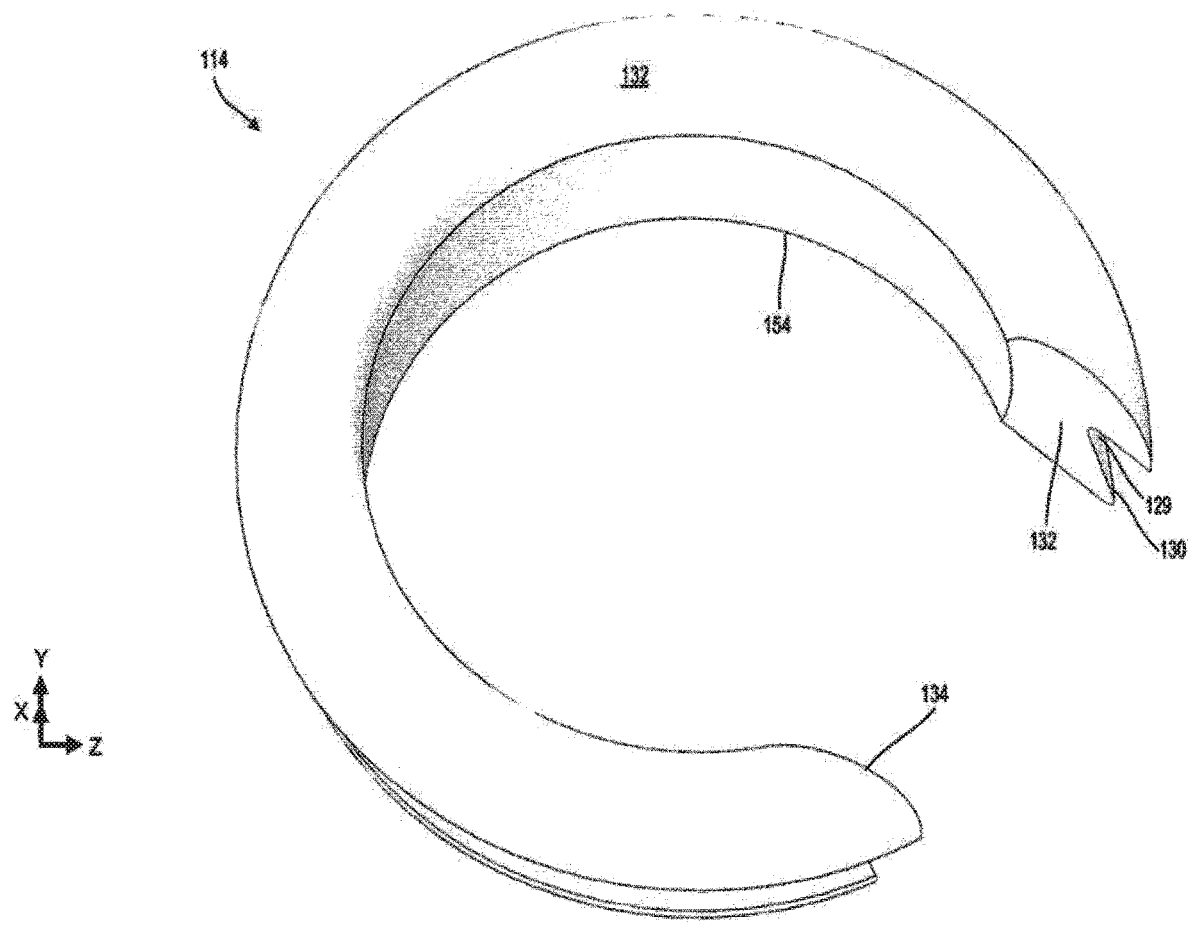
FIG. 5 is a perspective view of a rim bearing of the hybrid bearing of FIG. 1.
Figure 6:
FIG. 6 is a perspective view of the locking component of FIG. 1.

FIG. 5 is a perspective view of rim bearing 114. While rim bearing 114 is shown as a single segment, it can include multiple segments that abut or fit together to line upper chamber 122 of acetabular cup 120. For example, rim bearing 114 can be in the shape of an arc having a circumferential groove 129 and angled, outer sidewall 130 extending downward beneath a lip 132. When inserted in upper chamber 122 of acetabular cup 102 (i.e., above polar bearing 108 in lower chamber 120), groove 129 and angled sidewall 130 fit with reverse tapered portion 116 (see, e.g., FIG. 10). As shown, rim bearing 114 is open-ended. This allows compression of rim bearing 114, for example by pressing open ends 134, 136 towards one another, to facilitate insertion of rim bearing 114 into acetabular cup 102.

The rim bearing can also include a locking component or keystone 106 ("locking component" and "keystone" may be used interchangeably hereafter with reference number 106). Locking component 106 biases rim bearing 114 outward against the interior surface of cup 102 to secure polar bearing 108 (and rim bearing 114) with cup 102. One or more locking components can be used to secure the polar bearing 108. In addition, one or more rim bearings can be used in combination with one or more locking components. In one embodiment, multiple rim bearing can be used with no locking component such that the multiple segments of the rim bearings abut against each other.

The rim bearing 114 and the interior surface of the rim bearing can be made out of a compliant material (e.g., PE, UHMWPE, PEEK, cross-linked UHMWPE, and PMMA). Rim bearing 114 accommodates edge loading of the femoral head and/or impingement of the femoral neck on an edge of component 100. UHMWPE is self-lubricating and relatively compliant, and will therefore not bind the head by virtue of diametral contact in the same way a conventional hard bearing would do. Therefore, in one example, the polar bearing can be made of cross-linked UHMWPE (harder material) and the rim-bearing can be made of uncross-linked UHMWPE (compliant material).

Locking component or keystone 106 (FIG. 6) fits between open ends 134, 136 and has the same or similar outer profile as rim bearing 114. For example, angled sidewall 138 and a groove 140 of keystone 106 are identical in shape, position, depth and angle (as appropriate) to sidewall 130 and groove 129 of rim bearing 114. Thus, rim bearing 114 and keystone 106 need not be aligned with any particular features of upper chamber 122 to fit with reverse tapered portion 116.

The angled sidewall 138 may include one or more protrusions (not shown) sized to mate with indentations, notches, or holes in reverse tapered portion 116 of cup 102, to provide rotational adjustability of rim bearing 114. For example, a series of indentations, notches, or holes (not shown) may be placed about reverse tapered portion 116 of cup 102 such that locking component 106, and thus rim bearing 114, may be selectively placed and fixed. It will be appreciated that other aspects of locking component 106's geometry may be different than what is shown in the drawings. Alternatively, the indentations, notches, or holes can be on the rim bearing 114 and the indentations can be on the cup 102.

In practice, rim bearing 114 may be inserted into cup 102 intra-operatively. As rim bearing 114 and locking component 106 form two or more circumferential segments, rim bearing 114 may be compressed, inserted into cup 102 and then displaced radially outward into reverse tapered portion 116. Locking component 106 may be inserted between open ends 134, 136 to complete the circumference of hybrid bearing 104 and maintain position of rim bearing 114 within cup 102. Locking component 106 locks rim bearing 114 outward and prevents radially inward displacement of rim bearing 114. In one aspect, locking component 106 is placed with cup 102 following insertion of rim bearing 114. Locking component 106 may be affixed to acetabular cup 102, to prevent rotational motion of rim bearing 114 relative to acetabular cup 102. This for example allows intra-operative placement and adjustment of a rim bearing that is not axially symmetric, but has varying geometries, such as raised or lowered areas on the rim. Axially asymmetric rim bearings might for example be used by a surgeon to tailor bearing alignment to the anatomy of an individual patient or to the existing alignment of other components in the hip device.

The locking component 106 may first be placed with cup 102, and alternately, permanently or temporarily affixed with cup 102, and rim bearing 114 then compressed, inserted into the cup and displaced outwards to abut and/or join with locking component 106 and cup 102. Reverse tapered portion 116 prevents dissociation of rim bearing 114 out of cup 102 by edge loading or distraction forces imposed by the femoral head.

In another aspect, locking component 106 and/or rim bearing 114 may include features that fit with features of upper chamber 122, such that a specific orientation between upper chamber 122 and locking component 106 rim bearing 114 must be achieved in order to secure rim bearing 114 and locking component 106 with acetabular cup 102.

Figure 7:
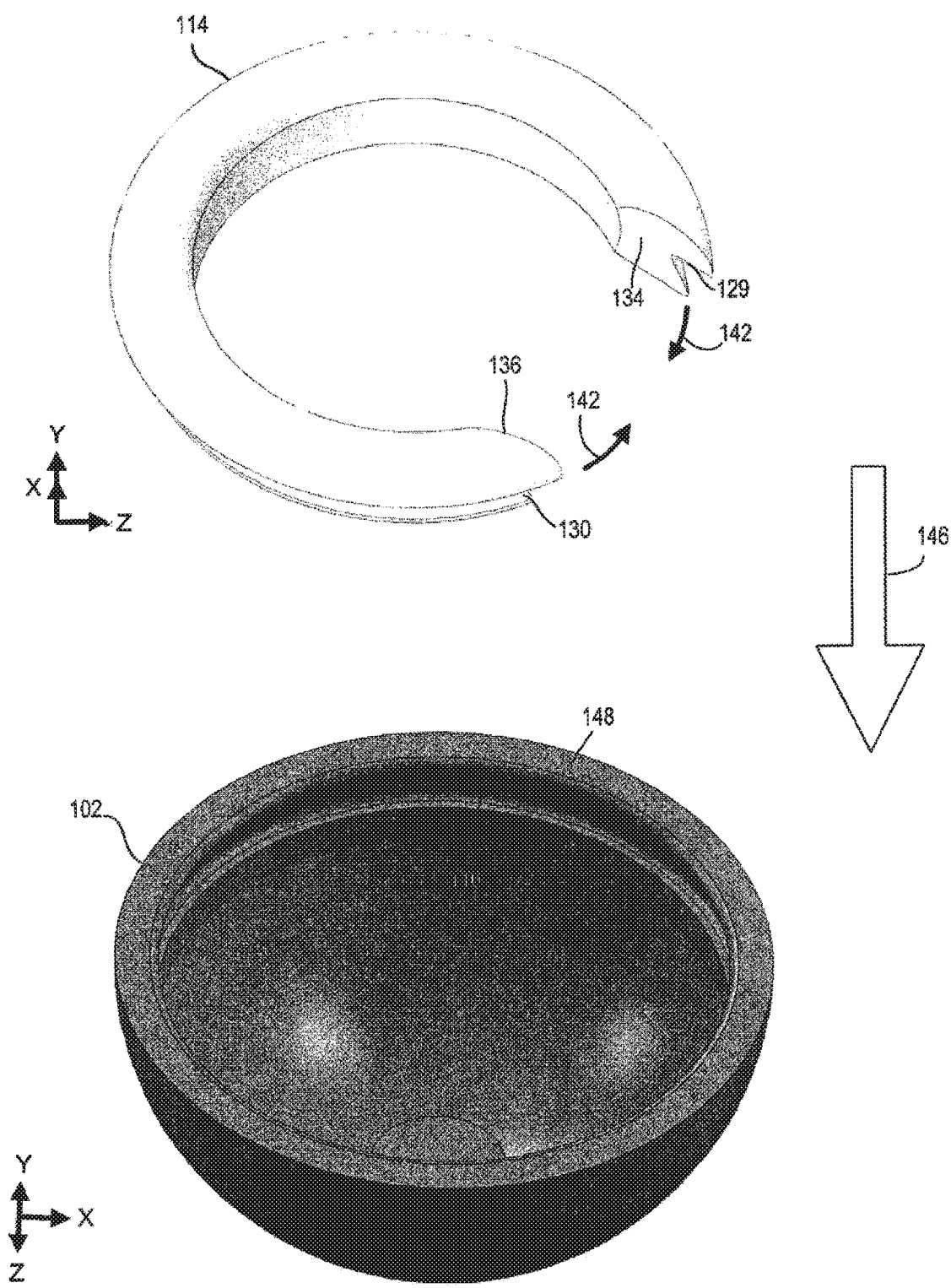
FIG. 7 is a perspective view illustrating inward compression of the rim bearing of FIG. 5 prior to insertion into the acetabular cup shown in FIGS. 1 and 2.

In practice, rim bearing 114 may be pinched or compressed to move open ends 134, 136 together, as indicated by arrows 142, FIG. 7, reducing the effective circumference of rim bearing 114 so that it can be inserted into upper chamber 122 (arrow 146), with groove 129 and angled sidewall 130 fitting with reverse tapered portion 116. Ends 134, 136 are released and allowed to spring or otherwise move out into alignment with the portion 116. Locking component 106 is inserted between ends 134, 136 and with its groove 140 and sidewall 138 conforming to reverse tapered portion 116. Locking component 106 biases or holds rim bearing 114 against reverse tapered portion 116, to lock bearing 114 in place. In addition, rim bearing 114 may itself be biased towards an "open" position such that it springs back to its original shape when ends 134, 136 are released. When in place, lip 132 of rim bearing 114 extends over a rim 148 of acetabular cup 102, covering cup rim 148 to prevent contact of a femoral head with hard cup rim 148. Likewise, a lip 144 of locking component segment 106 covers cup rim 148 when inserted into acetabular cup 102. Preventing contact between the femoral head and hard rim 148 may reduce or eliminate wear stripes caused by edge loading of conventional ceramic-on-ceramic hips, and may further interrupt the roll/slide vibration mechanism that contributes to in vivo squeaking.

Rim bearing 114 and locking component segment 106 may be sized to extend to greater than hemispherical coverage of the femoral head, thereby constraining the femoral head against distraction or micro-separation during gait and further mitigating detrimental effects of edge loading.

Forming rim bearing 114 of a relatively compliant material may allow an interference fit of the femoral head into a sub-hemispherical outer opening of the rim bearing during reduction of the hip in surgery. The rim bearing 114 can be designed to prevent the femoral head from separating from the polar bearing. The rim bearing can be designed such that it does not constrain the femoral head in the polar bearing.

In the case where the polar bearing 108 and rim bearing 114 are of unitary design to form the hybrid bearing 104, then a locking component may not be necessary.

Assembly of the Acetabular Component

Figure 8:
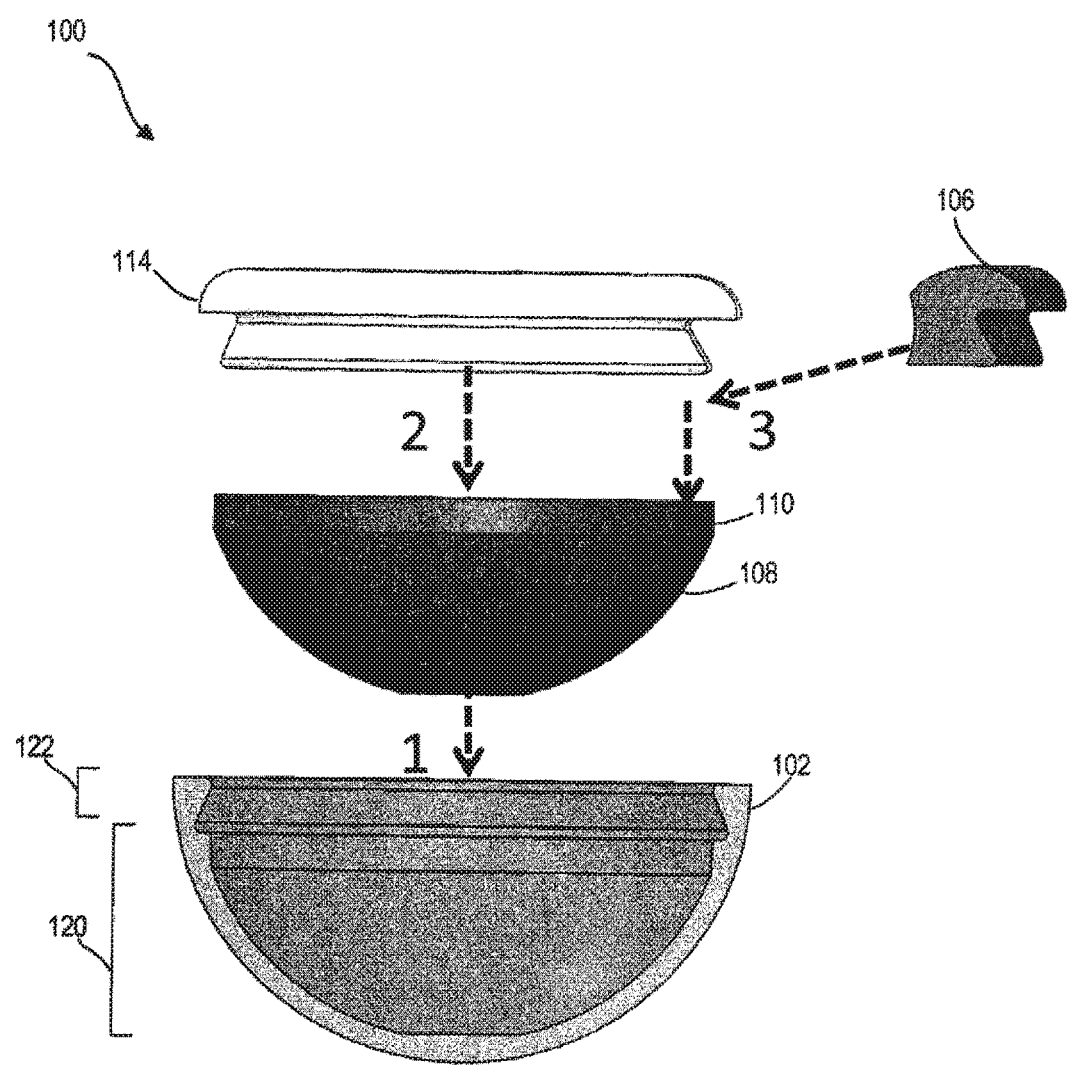
FIG. 8 is a pre-assembly side view of the acetabular component of FIG. 1.
Figure 8:
Figure 9:
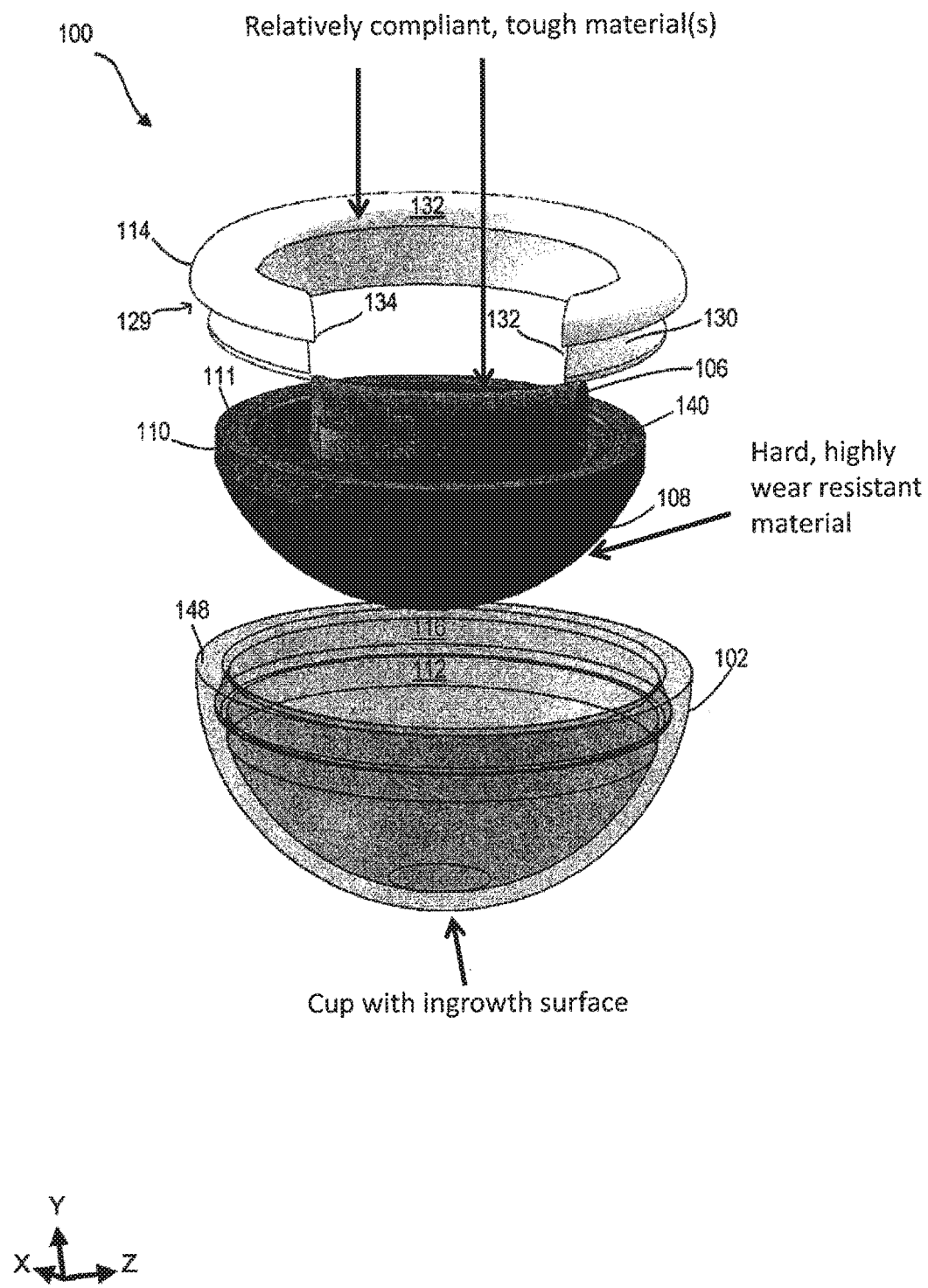
FIG. 9 is a pre-assembly perspective view of the acetabular component of FIGS. 1 and 8.

FIG. 8 schematically illustrates exemplary assembly of component 100. Polar bearing 108 is inserted into acetabular cup 102. Rim bearing 114 is next inserted into cup 102, above rim 111 of polar bearing 108 to form the hybrid bearing 104. If the rim bearing is of a design having open ends, then the free ends 134 and 136 are pressed towards one another to reduce effective circumference of rim bearing 114 and to facilitate alignment of groove 129 and angled sidewall 130 with reverse tapered portion 116. Once rim bearing 114 is inserted into cup 102 against portion 116 and with lip 132 covering cup rim 148, locking component 106 is inserted between free ends 134 and 136. FIG. 9 further illustrates alignment of locking component 106 with a gap between free ends 134 and 136. When no locking component is used, the rim bearing is a single component that is inserted into the cup 102 above rim 111 of polar bearing 108.

Figure 10:
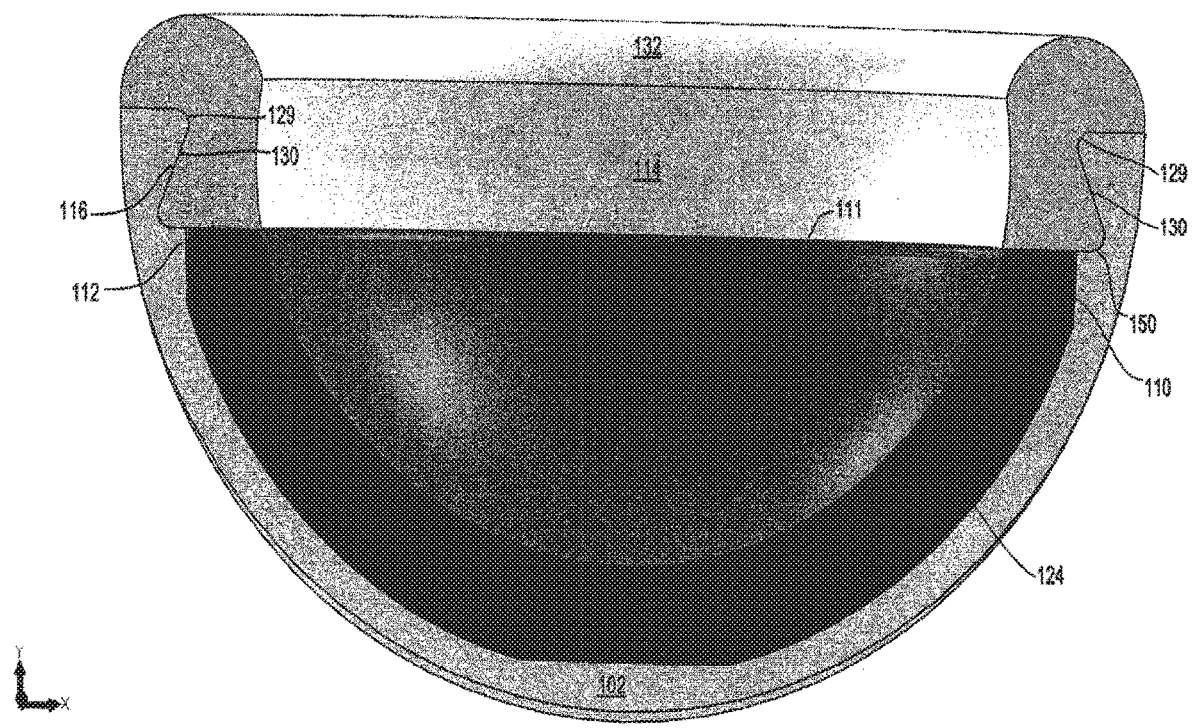
FIG. 10 is a cross-sectional view of an acetabular component, taken along line A-A of FIG. 1.

FIG. 10 is a cross-sectional view of an assembled hybrid bearing surface acetabular component, taken along line A-A, FIG. 1 and illustrating fit of edge 110 of polar bearing 108 against morse taper type profile 112 of cup 102 and fit of rim bearing 114 with and above reverse taper portion 116 of cup 102. As shown, rim 111 of polar bearing 108 and a mid-lip 150 of cup 102 may provide combined support for rim bearing 114 when inserted in cup 102 atop polar bearing 108.

Figure 11:
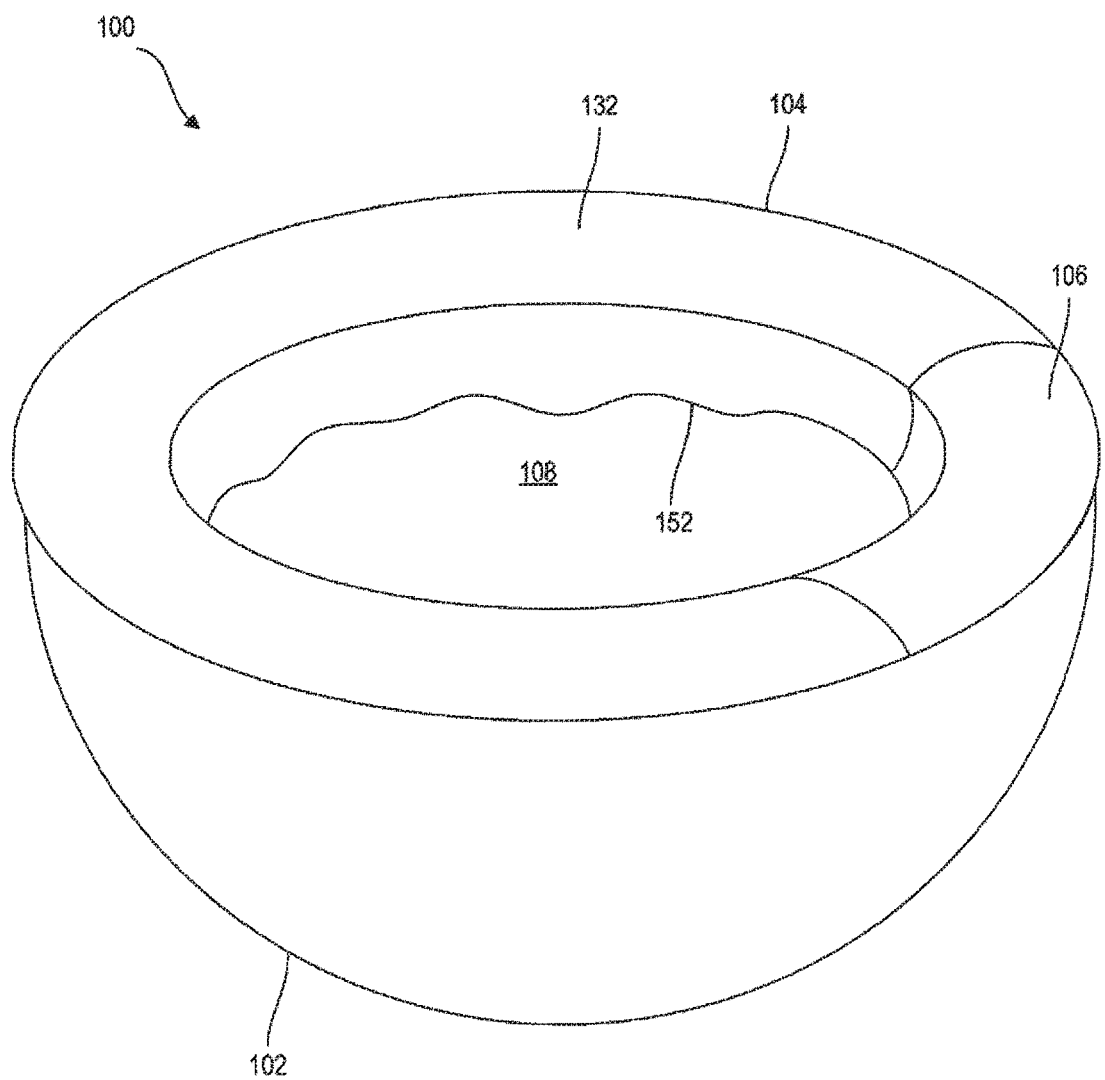
FIG. 11 is a perspective view of the acetabular component of FIG. 1, including an irregular boundary between a polar bearing and a rim bearing of the polar bearing.

As schematically shown in FIG. 11, the interior surface of polar bearing 108 of hybrid bearing 104 and the interior surface of rim bearing 114 may form a circumferential boundary. This boundary can be straight or be undulating. The undulating boundary can be formed by intercalation of the interior surfaces of the polar bearing 108 and rim bearing 114. Alternatively, the undulating boundary can be formed by interdigitation of complementary parts of the interior surfaces of the polar bearing 108 and rim bearing 114. The boundary can be an irregular boundary 152 when polar bearing 108 and rim bearing 114 are in place within cup 102. Rim 111 of polar bearing 108 and a base 154 of rim bearing 114 (see FIG. 5) may include complementary undulations, surface features and/or lock and key features to further secure the hybrid bearing 104 together. A base of locking component element 106 (base not shown) may include features similar to base 154 to provide continuous base geometry, or the locking component element 106 base may include unique surface features for alignment with a particular and complimentary area of rim 111 of polar bearing 108. Irregular boundary 152 may provide a smooth, less abrupt transition of the femoral head between bearing materials, thus reducing stress concentration. Locating the boundary between rim bearing 114 and polar bearing 108 within acetabular cup 102 further manages stress concentration. Alternately or additionally (and regardless of boundary 152 regularity or irregularity), rim bearing 114 may be designed with a smaller radius of curvature internal diameter than polar bearing 108, allowing rim bearing 114 to stand proud of polar bearing 108 at the interface between the two. Thus, the relatively tougher, more compliant material of rim bearing 114 (as opposed to polar bearing 108) accepts the burden of any stress increase that might be caused by the boundary between bearing materials. Rim bearing 114 may also have a tighter radius of curvature in the "z" direction than polar bearing 108, thereby curving into the femoral head and holding it against articular surface 128 to prevent the femoral head from rolling up and outward. The hybrid bearing surface can also include a groove between the interior surfaces of the polar bearing and the rim bearing for collecting debris.

Figure 12:
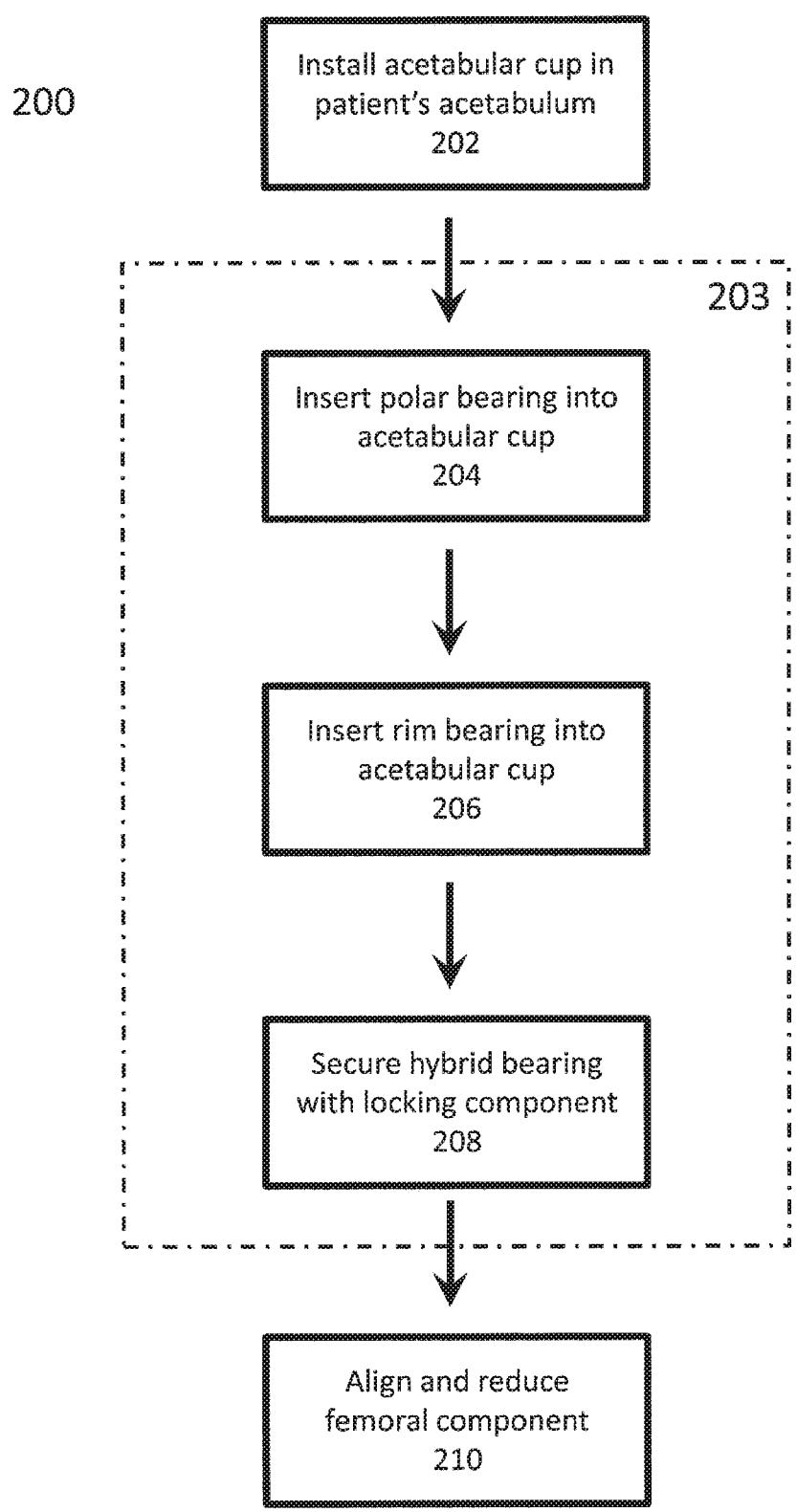
FIG. 12 is a flowchart illustrating a method of installing a prosthesis where the polar bearing and the acetabular cup are separate components.

Method for Installing a Prosthesis where the Polar Bearing and the Acetabular Cup are Separate Components The invention features methods for installing in a patient, a prosthesis that includes a hybrid bearing surface acetabular component. FIG. 12 shows an exemplary method 200 for installing an artificial hip. In step 202, an acetabular cup is placed and secured with a patient's acetabulum, e.g., using bone cement or other medium or methods known in orthopedic surgery. A hybrid bearing component is placed within the acetabular cup in steps 202-208 (outlined by dotted box 203). In step 204, the polar bearing is inserted into the acetabular cup such that outer surfaces of the polar bearing contact or approximate an inner base and surfaces of the acetabular cup. The exterior of the polar bearing may be complementary to the interior of the acetabular cup, for example having a bowl or cup shape.

In step 206, a rim bearing is inserted into the acetabular cup such that a base of the rim bearing rests upon a rim of the polar bearing thus forming the hybrid bearing. A lip of the rim bearing can overlap a rim of the acetabular cup. Insertion of the rim bearing may include compressing ends of the rim bearing together to reduce effective circumference of the rim bearing, and advancing the rim bearing into the acetabular cup. Where the rim of the polar bearing and the base of the rim bearing include complementary lock and key or other alignment features, the rim bearing is placed with the polar bearing in a specific orientation.

If the rim bearing is open ended, then one or more locking components is inserted between open ends of the rim bearing in step 208. In this case, a lip of the locking component overlaps the rim of the acetabular cup left exposed between the open ends of the rim bearing. The locking component may be pushed or snapped into place between the open ends. Optionally, protrusions (i.e., lugs) on an outer surface of the locking component are aligned with select holes or indentations of a series of holes or indentations lining at least a portion of the acetabular cup, to customize position of the rim bearing and locking component and to prevent rotation of the rim bearing (and optionally, the entire hybrid bearing) within the cup, once the locking component is in place. Still optionally or alternatively, an adhesive may be used to secure locking component in place with respect to the acetabular cup.

Following placement of the hybrid bearing component, and optionally, any drying time, the head of the femoral component is aligned with the socket formed by the hybrid bearing, and the femoral component is reduced into the socket, in step 210.

The steps of inserting the hybrid bearing surface component (box 203) may vary in order. For example, the locking component may be placed with the acetabular cup and above the polar bearing (and optionally affixed with the acetabular cup) before placement of the rim bearing. Method 200 shown in FIG. 12 does not specify pre-placement steps of surgery, placement of a femoral head with the femur or other routine surgical steps (e.g., suction, cleaning and closure).

Intra-operative placement of polar bearing 108 with acetabular cup 100 allows a surgeon to customize placement of locking component 106 and/or rim bearing 114 with respect to acetabular cup 102. For example, rim bearing 114 may be axially asymmetrical to allow a surgeon to establish a best fit with other hip device components or with individual anatomy. The acetabular cup 102 can be pre-assembled with polar bearing 108 and rim bearing 114, such that the entire hybrid bearing surface acetabular component 100 may be placed and affixed as a single unit.

Method for Installing a Prosthesis where the Polar Bearing is Integral to the Acetabular Cup FIG. 13 shows an exemplary method 300 of installing an artificial hip where the polar bearing is integral to the acetabular cup. For example, the polar bearing 108 may be omitted and its geometry machined into or otherwise formed with the acetabular cup. The acetabular cup itself thus provides a circumferential inner shelf or ledge to support a circumferential base of the rim bearing (i.e., rim bearing 114). The inner ledge may include surface features or geometry for mating with base features of the rim bearing, to further enhance fit and security of the rim bearing within the acetabular cup.

In step 302, an acetabular cup is placed and secured with a patient's acetabulum, for example using bone cement or other known medium or method. A rim bearing is inserted into the acetabular cup in step 304, and a locking component inserted in step 306. In one example of steps 304 and 306, open ends of rim bearing 114 are pressed together to reduce effective circumference of the rim bearing, and the rim bearing is placed with an upper chamber of the acetabular cup (similar to chamber 122 of cup 102). Rim bearing 114 for example rests upon an internal circumferential shelf or edge machined into the acetabular cup. Exterior groove 129 and sidewall 130 of the rim bearing may be fitted against a reverse tapered portion of the upper chamber (similar to reverse tapered portion 116 of cup 102). When in place, lip 132 of rim bearing 114 covers a rim of the cup (similar to rim 148) to prevent contact between the hard cup rim and a femoral component. Locking component 106 is placed in the upper cup chamber between open ends of the rim bearing. The external surface features (e.g., protrusions) can be selectively mated with complementary mating features (e.g., indentations, notches or holes) inside the cup, for customizing position of the rim bearing and keystone element with the cup. When in place, lip 144 of locking component 106 covers the cup rim. The femoral head is aligned with the acetabular cup and rim bearing and reduced into place, in step 308.

Method for Installing a Prosthesis that Includes the Use of a Rim Pad/Apron

Figure 14:
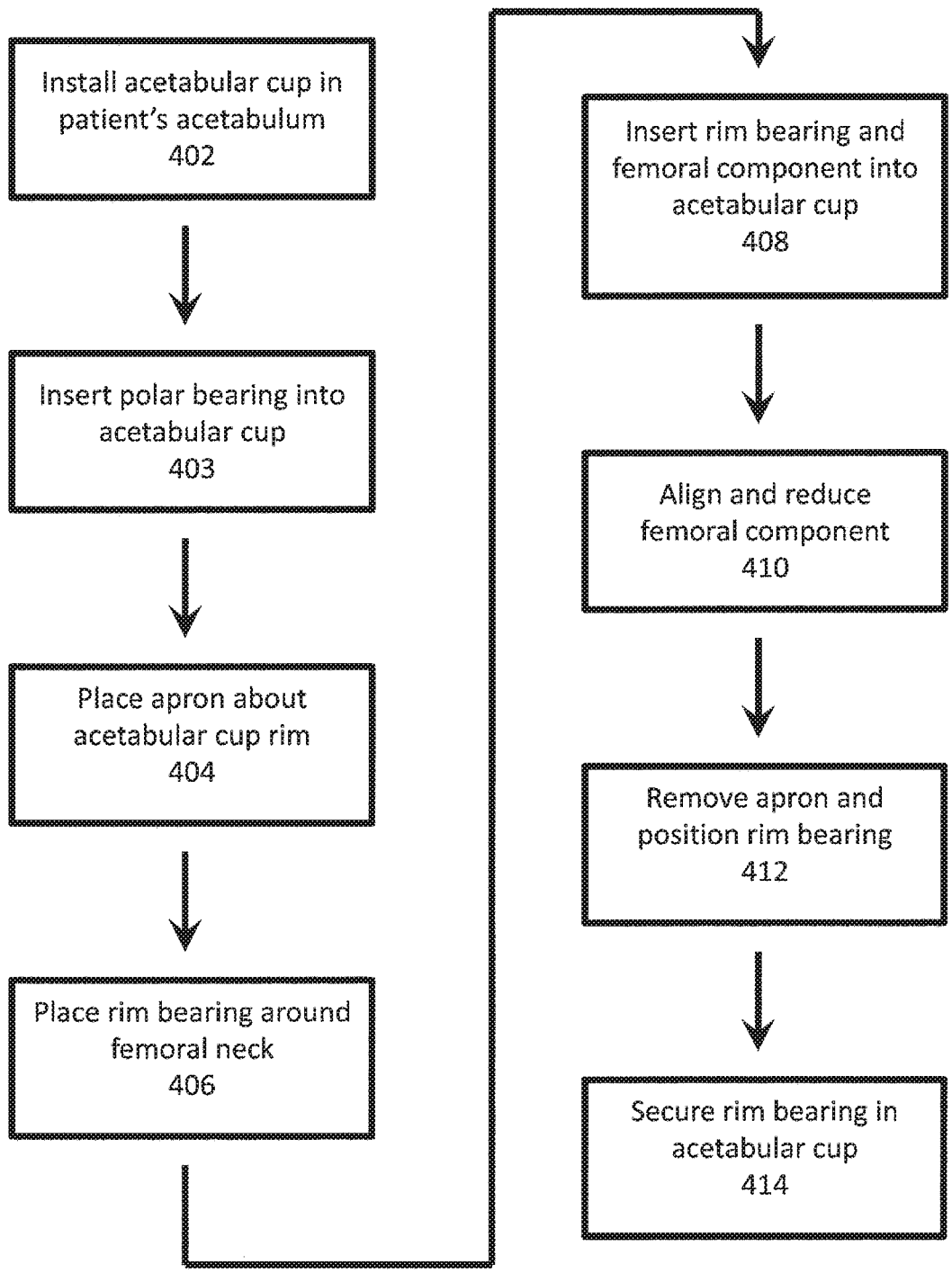
FIG. 14 is a flowchart showing a method of installing a prosthesis that includes the use of a rim pad/apron.

FIG. 14 shows an alternative method 400 of installing an artificial hip. An acetabular cup is placed and secured with a patient's acetabulum in step 402. A polar bearing 108, is inserted into the cup in optional step 403. Step 403 may not be necessary where the polar bearing is machined into or otherwise integral to the acetabular cup. In step 404, the cup rim is padded to prevent contact of a femoral head on the hard cup rim. In one example of step 404, a temporary protective apron of a strong and resilient material is placed about the cup rim. The apron is, for example, a thin sheet of material that has high toughness and a low coefficient of friction, and is flexible in sheet form. Thus, the apron provides a non-damaging, low friction path for the femoral head to move from its dislocated position, over the hard cup rim and into its fully reduced position in the bearing. Exemplary apron materials include UHMWPE, high density PE, low density PE, polyoxymethylene and its derivatives (e.g., Delrin™), polyamides (i.e., nylons), polypropylene, and other polymers. The apron may be shaped as an annular ring. Alternately, the apron may form a "c" shape with the opening of the "c" ranging from a small slit to a larger opening. Where the apron is a "c" shape, step 404 includes placing the opening away from the direction of approach of the femoral head during reduction.

A rim bearing is placed with a femoral component, in step 406, and the femoral head is then attached to the femoral neck. In one example, rim bearing 114 is placed about the femoral neck prior to nailing or otherwise attaching the femoral neck to the femoral head.

The femoral head is aligned with the acetabular cup and reduced into place, in step 408 and 410. The apron or other padding about the cup rim prevents contact between the femoral head and the rim during reduction. Once reduction is satisfactorily completed, the padding is removed, in step 412. In one example of step 412, an annular ring apron is cut through and removed. In another example of step 412, a "c" shaped apron is pulled from the cup.

The rim bearing is positioned about the cup rim, in step 408. In one example of step 410, rim bearing 114 is drawn onto the rim of the cup and secured in place, in step 414. In one example of step 414, the rim bearing is secured in place using a locking component, as described herein. In another example of step 414, the rim bearing 114 is a continuous ring, and a locking component such as element 106 is not used to secure the bearing in place. Rather, complementary lock-and-key features between the rim bearing and acetabular cup may be mated together to secure the rim bearing in place, a fixative may be used and/or geometry and elastic properties of the rim bearing may bias the rim bearing against the acetabular cup.

The steps of the above described methods can vary in order and the order of assembling various components in situ can be determined based on the design of the acetabular component and on surgical techniques.

Figure 15:
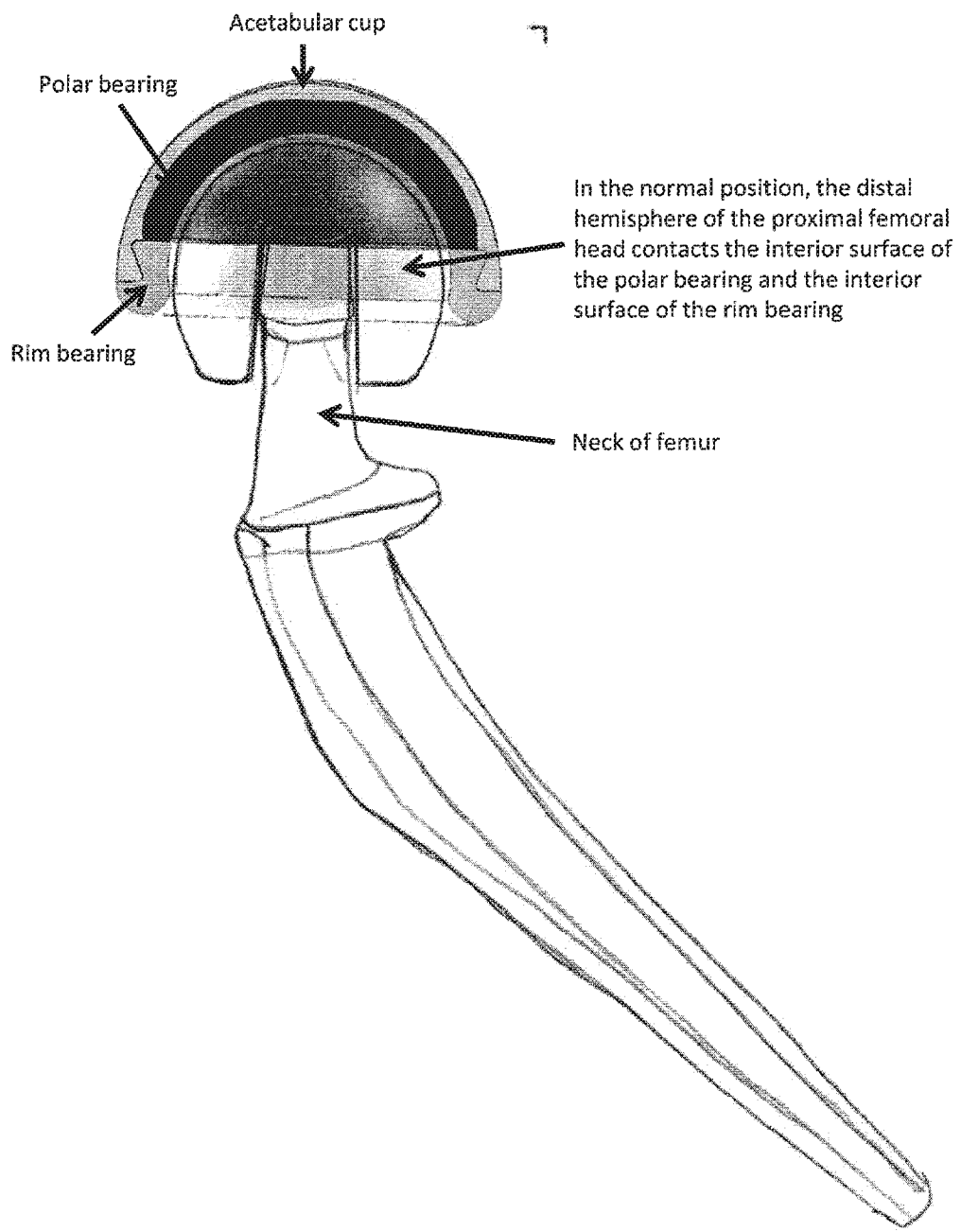
FIG. 15 is a cross-sectional view showing the femoral head reduced in position in the acetabular component. In this normal position, the axis of the femoral head originating from the femoral neck and passing through the pole of the polar bearing is parallel to the axis of the polar bearing, and the distal hemisphere of the proximal femoral head can contact the interior surface of the polar bearing and the interior surface of the rim bearing.

FIG. 15 shows the femoral head reduced in place in the acetabular cup. As seen in the cross-section view, the distal hemisphere of the proximal femoral head, which is the hemisphere of the proximal femoral head that is farthest away from the neck of the femur, can contact the interior surface of the polar bearing and the interior surface of the rim bearing.

Rim Bearing Insertion Tool

The invention also features a rim bearing insertion tool for inserting a rim bearing above a polar bearing of an acetabular component. The tool can include: a) means for removably securing the tool to the acetabular cup; b) means for reversibly engaging the rim bearing onto the tool for placement into the acetabular cup; c) means for reducing the effective diameter of the rim bearing; d) means for inserting the rim bearing into the acetabular cup; and e) means for mutually aligning the rim bearing and a locking component to place the locking component in a location suitable for insertion and locking of the rim bearing.

Figure 16:
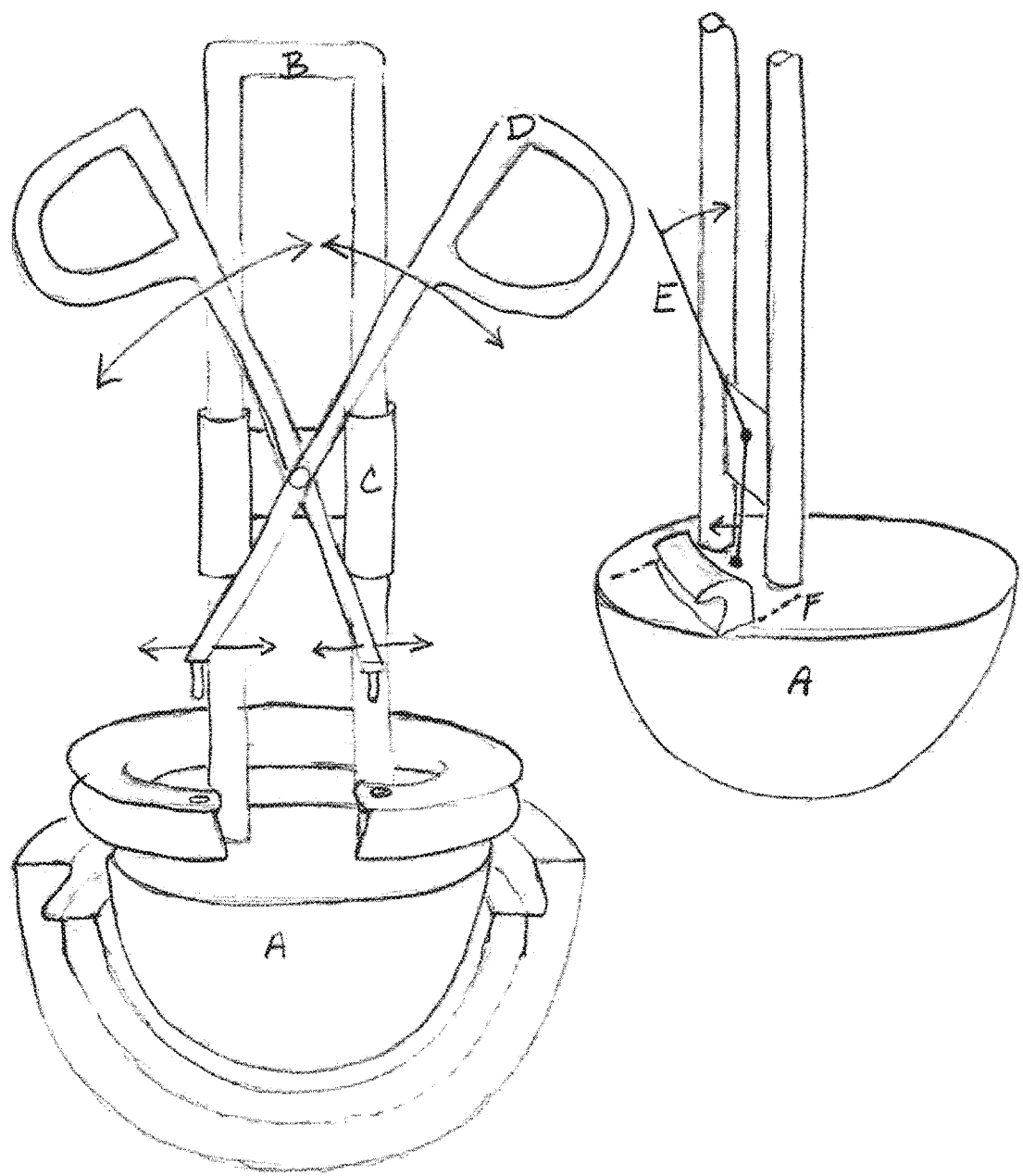
FIG. 16 shows a rim bearing insertion tool that can be used for inserting the rim bearing into the acetabular cup.

FIG. 16 shows an exemplary rim bearing insertion tool that can be used for inserting the rim bearing into the acetabular cup. The tool can include a base (A) and a frame (B) that extends from the top of the base. The base of the tool can have a shape that is compatible with the polar bearing, is self-centering, and is stable in that location so that it does not damage the polar bearing surface when rotated within the polar bearing. For example, as shown in FIG. 16, the tool can include a base that is substantially hemispherical in shape (A) and can be made of a relatively soft material (e.g. UHMWPE or thermoplastic) that can allow the tool to be centered in the already-installed acetabular cup and polar bearing. The base can also be a segment of a sphere, i.e., more or less than a hemisphere such that a part of it can fit into the polar bearing and/or the acetabular cup. The base can also be a shape that has a spherical outline. Alternatively, the base can have a blunt or rounded tip, or have arc shaped extensions or protrusions that follow a hemispherical shape that is compatible with the polar bearing. The top surface of the base can act as a floor, or 'stop' for the rim bearing at the correct height, when the base sits at or below the top rim of the installed polar bearing.

The base of the tool is desirably made of a material that is of a lesser hardness than that of the polar bearing in order to avoid damage to the polar bearing during installation. Exemplary materials that can be used to make the base of the tool are PE, UHMWPE, PMMA, and polyoxymethylene and its derivatives (e.g., Delrin™). In one example, the base of the tool is stainless steel when the polar bearing is made of a ceramic material.

Extending from the top of the base is a frame (B) that can be made, e.g., of stainless steel and serves as a handle and a manual rotational alignment mechanism. A sliding carriage (C) is allowed to travel up and down the stainless steel frame. Affixed to the sliding carriage is a scissors mechanism (D) with appropriate handles for manual inward and outward manipulation on the upper part, and downward pointing pins on the lower part. The pins can fit into appropriately sized holes manufactured in the rim bearing, one near each end of the 'c' shape. The rim bearing insertion tool can be sterilized before and after surgery.

The sequence of assembling a prosthesis in a patient using the rim bearing insertion tool can include the following steps: a) removably securing the tool to an acetabular cup installed in a patient; b) reversibly engaging the rim bearing onto the tool; c) reducing the effective diameter of the rim bearing; d) inserting the rim bearing into the acetabular cup; e) mutually aligning the rim bearing and a locking component; and f) placing the locking component in a suitable location to lock the rim bearing.

The sequence of assembling a prosthesis in a patient using the rim bearing insertion tool can also include the following steps (e.g., when using a tool, such as the one shown in FIG. 16): a) the acetabular cup with the polar bearing inserted can be implanted in the acetabulum by methods described above; b) The rim bearing can be fitted around the stainless frame of the insertion tool, on top of the hemispherical base (this step can be performed on a back table); c) the rim bearing can be rotated to align with the pins in the scissors mechanism and pressed onto the pins; d) The insertion tool can be placed in the acetabular polar bearing; e) the scissor mechanism can be squeezed together to contract the rim bearing to a smaller effective diameter; f) The sliding carriage can be pushed down until the rim bearing is adjacent to, and inside of, the reverse taper on the acetabular cup; g) the scissor mechanism can be opened and allow the rim bearing to deflect radially outward into the reverse taper profile of the acetabular cup; h) the locking component can be placed onto the hemispherical base directly adjacent to the opening; i) the locking component can be pushed radially into its opening; j) the travelling carriage can be raised, pulling the pins form the holes in the rim bearing; and k) the instrument can then be pulled out of the surgical site.

If needed, in step h), alignment guides can be placed along dotted lines as shown by (F) to more precisely place the keystone element at the opening. With the scissors mechanism pins still engaged in the rim bearing, the rotational alignment of the keystone element to its opening is assured. Furthermore, in step i), the pushing of the locking component can be done with more force using a lever mechanism as shown by (E). Alternatively, outward radial force on the keystone element can be supplied by expanding pliers, one element of which can react against the base of the steel frame/handle.

In practice it may be easier to tilt the rim bearing slightly such that the center part of the 'c' (away from the split) can be inserted into the reverse taper profile first, and then the split ends of the bearing can be brought down. This instrument design can allow for that tilting, either by manually pushing the center part of the rim bearing downward, or by tilting the entire instrument relative to the axis of the acetabular cup. The hemispherical base can allow for this while maintaining center position and rotational alignment.

Other Embodiments

While the present invention has been described above, it should be clear that many changes and modifications may be made to the component and related methods without departing from the spirit and scope of this invention. Likewise, features described with respect to a disclosed method may also apply to components and systems herein, and vice versa.

The invention claimed is:

1. An acetabular component comprising a hybrid bearing, the hybrid bearing configured to fit into an acetabular cup, the hybrid bearing comprising:
   (a) a polar bearing;
   (b) a rim bearing, wherein the rim bearing is arc-shaped to allow reduction in effective circumference of the rim bearing and to facilitate insertion of the rim bearing into the acetabular cup; and
   (c) a locking component for securing the rim bearing radially against the acetabular cup, wherein the locking component fits between two ends of the arc-shaped rim bearing to secure the rim bearing against the acetabular cup;
   wherein the rim bearing or the locking component comprises an alignment element for aligning the rim bearing and the locking component with the acetabular cup, and wherein an interior surface of the polar bearing and an interior surface of the rim bearing form a hybrid bearing surface configured to contact a proximal femoral head.

2. The acetabular component of claim 1, wherein the alignment element is an interdigitation of a circumferential boundary between the polar bearing and the rim bearing and/or locking component.

3. The acetabular component of claim 1, wherein the alignment element comprises one or more protrusions on the rim bearing, wherein the one or more protrusions are sized to mate with holes, notches, or indentations on the acetabular cup.

4. The acetabular component of claim 1, wherein the alignment element comprises one or more protrusions on the locking component, wherein the one or more protrusions are sized to mate with holes, notches, or indentations on the acetabular cup.

5. The acetabular component of claim 1, wherein the rim bearing comprises a lip for covering a rim of the acetabular cup.

6. The acetabular component of claim 1, wherein the locking component comprises a lip for covering a rim of the acetabular cup between the ends of the arc-shaped rim bearing.

7. The acetabular component of claim 1, wherein the acetabular cup comprises a reverse tapered portion on an inner circumference.

8. The acetabular component of claim 1, wherein the acetabular cup comprises a morse taper present about an inner circumference of the acetabular cup.

9. A method for installing in a patient a prosthesis comprising an acetabular component and an acetabular cup, the acetabular component comprising a hybrid bearing, the hybrid bearing configured to fit into the acetabular cup, the hybrid bearing comprising:
   (a) a polar bearing;
   (b) a rim bearing, wherein the rim bearing is arc-shaped to allow reduction in effective circumference of the rim bearing and to facilitate insertion of the rim bearing into the acetabular cup; and
   (c) a locking component that fits between two ends of the arc-shaped rim bearing; said method comprising:
   (i) installing the acetabular cup in an acetabulum of the patient;
   (ii) inserting the polar bearing into the acetabular cup;
   (iii) inserting the rim bearing into the acetabular cup, wherein an interior surface of the polar bearing and an interior surface of the rim bearing form a hybrid bearing surface configured to contact a proximal femoral head,
   (iv) aligning and reducing the proximal femoral head, wherein a distal portion of the proximal femoral head contacts the polar bearing and the rim bearing, and
   (v) after step (iii), and before or after step (iv), installing the locking component, thereby securing the rim bearing radially against the acetabular cup.

10. The method of claim 9, wherein the rim bearing is aligned with the polar bearing in the acetabular cup by forming a complementary interdigitation of the interior surface of the polar bearing and the interior surface of the rim bearing.

11. The method of claim 9, wherein the rim bearing is aligned with the acetabular cup by mating a plurality of holes, notches, or indentations on the acetabular cup with one or more protrusions on the rim bearing.

12. The method of claim 9, wherein the locking component is aligned with the acetabular cup by mating a plurality of holes, notches, or indentations on the acetabular cup with one or more protrusions on the locking component.

13. A method for installing in a patient a prosthesis comprising an acetabular component and an acetabular cup, the acetabular component comprising a hybrid bearing, the hybrid bearing configured to fit into an acetabular cup, the hybrid bearing comprising:
   (a) a polar bearing;
   (b) a rim bearing, wherein the rim bearing is arc-shaped to allow reduction in effective circumference of the rim bearing and to facilitate insertion of the rim bearing into the acetabular cup; and
   (c) a locking component that fits between two ends of the arc-shaped rim bearing; said method comprising:
   (i) installing the acetabular cup in an acetabulum of the patient;
   (ii) inserting the polar bearing into the acetabular cup;
   (iii) placing an apron about the rim of the acetabular cup;
   (iv) placing the rim bearing around a femoral neck;

(v) attaching a femoral head to the femoral neck to form a femoral component;
(vi) inserting the rim bearing and the femoral component into the acetabular cup, wherein an interior surface of the polar bearing and an interior surface of the rim bearing form a hybrid bearing surface configured to contact the femoral head;
(vii) aligning and reducing the femoral head of the femoral component, wherein a distal portion of the femoral head contacts the polar bearing and the rim bearing;
(viii) removing the apron;
(ix) positioning the rim bearing in the acetabular cup; and
(x) installing the locking component, thereby securing said rim bearing in said acetabular cup.

14. The method of claim 13, wherein the apron is made from a material selected from the group consisting of UHMWPE, low density PE, polyoxymethylene, nylon, and polypropylene.

15. The method of claim 13, wherein the apron is in the shape of a circle or an arc.

* * * * *